United States Patent [19]

Hofmeister et al.

[11] 4,277,468
[45] Jul. 7, 1981

[54] 11-METHYLENE STEROIDS, THEIR PREPARATION AND PHARMACEUTICAL PREPARATIONS CONTAINING THEM

[75] Inventors: Helmut Hofmeister; Rudolf Wiechert; Klaus Annen; Henry Laurent; Hermann Steinbeck, all of Berlin, Fed. Rep. of Germany

[73] Assignee: Schering Aktiengesellschaft, Berlin and Bergkamen, Fed. Rep. of Germany

[21] Appl. No.: 135,066

[22] Filed: Mar. 28, 1980

[30] Foreign Application Priority Data

Mar. 30, 1979 [DE] Fed. Rep. of Germany ....... 2913381

[51] Int. Cl.$^3$ ............................................. C07J 1/00
[52] U.S. Cl. ................................ 424/243; 260/397.45; 260/397.5
[58] Field of Search ............. 260/397.4, 397.45, 397.5; 424/243

[56] References Cited

U.S. PATENT DOCUMENTS 3,927,046  12/1975  van den Broek ................ 260/397.45

OTHER PUBLICATIONS

Fried et al., JACS 83 (1961), pp. 4663-4464.

Primary Examiner—Elbert L. Roberts
Attorney, Agent, or Firm—Millen & White

[57] ABSTRACT

11-Methylene steroids of Formula I

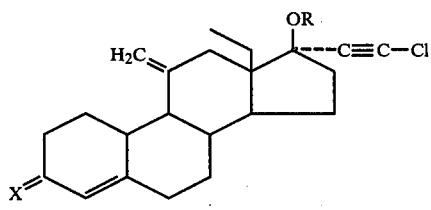

wherein
R is hydrogen or acyl, and
X is oxygen or two hydrogen atoms
have valuable pharmacological properties.

10 Claims, No Drawings

11-METHYLENE STEROIDS, THEIR PREPARATION AND PHARMACEUTICAL PREPARATIONS CONTAINING THEM

BACKGROUND OF THE INVENTION

The present invention relates to 11-methylene steroids, a process for their preparation, and pharmaceutical preparations containing them.

It is known that 11-methylene steroids possess valuable biological properties. For example, DOS [German Unexamined Laid-Open Application] No. 2,361,120 describes 11-methylene-17α-ethynyl-18-methyl-Δ$^4$-estrenes possessing strong progestational properties.

SUMMARY OF THE INVENTION

It is an object of this invention to provide new steroidal compounds having valuable pharmacological properties.

Upon further study of the specification and appended claims, further objects and advantages of this invention will become apparent to those skilled in the art.

These objects have been attained by providing 11-methylene steroids of Formula I

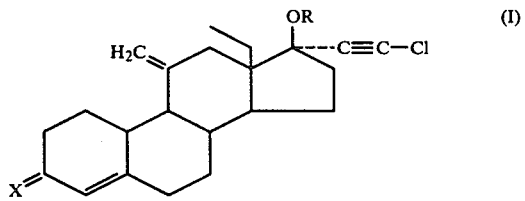

wherein
R is hydrogen or acyl, and
X is oxygen or two hydrogen atoms.

DETAILED DISCUSSION

The steroids of Formula I contain the group OR in the 17β-position, wherein R is hydrogen or an acyl group. Suitable acyl groups R are those of acids which form resultant physiologically compatible steroids, e.g., such acids which are $C_{1-17}$ hydrocarbon carboxylic or sulfonic acids. Preferred acids which are equivalent include the former, e.g., organic carboxylic and sulfonic acids of 1–17 carbon atoms belonging to the aliphatic, cycloaliphatic, aromatic or aromatic-aliphatic series or such acids belonging to the heterocyclic series. These acids can also be saturated or unsaturated, mono- or polybasic and/or substituted in conventional fashion for such acyl forming acids producing further equivalent acids and resultant acyl groups. Examples of such substituents include hydroxy, alkoxy, acyloxy, oxo, amino and halogen.

The following equivalent carboxylic acids can be mentioned as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, β-cyclopentylpropionic acid, cyclohexylacetic acid, cyclohexanecarboxylic acid, phenylacetic acid, phenoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid, furan-2-carboxylic acid, O-tridecanoylglycolic acid, O-hexadecanoylglycolic acid, β-tridecanoyloxypropionic acid, etc. Suitable sulfonic acids include: methane-, ethane-, β-chloroethane-, propane-, isopropane-, butane-, cyclopentane-, cyclohexane-, benzene-, p-toluene- and p-chlorobenzenesulfonic acids, etc.; and, furthermore, N,N-dimethyl-, N,N-diethyl, bis(β-chloroethyl)-aminosulfonic acids, etc.; or pyrrolidino, piperidino-, piperazino-, N-methylpiperazino-, morpholinosulfonic acids, etc.

The compounds of this invention can be prepared by reacting an 11-methylene-17-oxo steroid of formula II

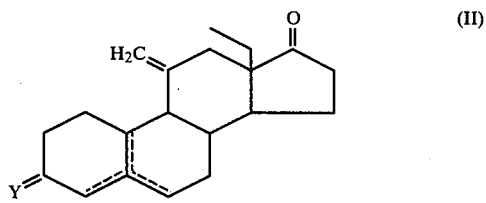

wherein Y is a free or acid-hydrolyzable blocked oxo group or two hydrogen atoms and

is a double bond in the 4,5-, 5,6- or 5,10-position, or two double bonds emanating from the 3- and 5-positions, according to methods known per se with an organometallic chloroethynyl compound to produce a compound of formula I wherein R is hydrogen; hydrolyzing an initially introduced 3-oxo blocking group; and, depending on the finally desired groups for R, optionally esterifying the 17-hydroxy group before or after the splitting off of the blocking group.

This process is conducted according to methods known per se by reacting the 17-oxo steroid in a suitable solvent with the organometallic chloroethynyl compound at a temperature of 0°–50° C. for 0.1–0.5 hours. The chloroethynyl compound may be formed in situ from 1,2-dichloroethylene and an ethereal alkyl lithium solution, such as, for example, methyl- or butyllithium solution. Suitable solvents include tetrahydrofuran and diethyl ether.

When a 3-keto group is present in II, it is suitably protected prior to chloroethynylation. The protective blocking group is to be cleavable by acid hydrolysis. The blocking group Y should form, with the double bond or double bonds present in ring A or B, such an arrangement of atoms that the compound will be converted into a 4,5-unsaturated ketone by subsequent acid hydrolysis. In a preferred embodiment, the keto group is blocked by ketal formation. The ketal residues are derived from the alcohols and thioalcohols conventionally utilized for the blocking of free oxo groups; examples in this connection include: ethylene glycol, 2,2-dimethyl-1,3-propanediol, 1,2-ethanedithiol, etc. The 3-keto group, however, can also be partially blocked by enol ether, enol ester, or enamine formation.

The splitting off of the 3-keto blocking group, which can be conducted before or after the optional esterification, can be effected according to methods known to those skilled in the art. Suitable agents for splitting purposes include, for example, mineral acids, e.g., perchloric acid, sulfuric acid, or hydrochloric acid, or organic acids, e.g., oxalic acid. The splitting step is preferably carried out in an alcoholic solution or in another polar solvent, such as, for example, acetone, at temperatures of about 20°–100° C.

For the optionally subsequent esterification, fully conventional processes normally employed in steroid chemistry for esterification can be used. One example is reaction with an acid or acid anhydride in the presence of strong acids, e.g., trifluoroacetic acid or p-toluenesulfonic acid, at room temperature or slightly elevated temperature. Another example is reaction with an acid anhydride in the presence of a tertiary amine while heating at about 20°–200° C. If pyridine and 4-(dimethylamino)pyridine are used together as the tertiary amines, the esterification can be conducted at room temperature.

The starting compounds of Formula II used in the process of this invention are described in DOS No. 2,361,120 or can be prepared analogously to the methods disclosed therein.

For example, a preferred starting material, 3,3-(2',2'-dimethyl-trimethylenedioxy)-18-methyl-11-methylene-5-estren-17-one can be prepared as follows.

1.0 g of 18-methyl-11-methylene-4-estrene-3,17-dione in 10 ml of methylene chloride is combined at room temperature with 1 ml of triethyl orthoformate, 2.0 g of 2,2-dimethyl-1,3-propanediol and 5 mg of p-toluenesulfonic acid. After 5 hours, the reaction mixture is diluted with methylene chloride, washed neutral, and dried. The crude product is chromatographed on silica gel with hexane-acetone (0–3%). Yield: 800 mg of 3,3-(2',2'-dimethyltrimethylenedioxy)-18-methyl-11-methylene-5-estren-17-one, m.p. 194° C.; $[\alpha]_D = +105.7°$.

It has now been found that the 17α-chloroethynyl compounds of this invention, which have not been described heretofore, exhibit a strong progestational efficacy, as do the corresponding 17α-ethynyl compounds of DOS No. 2,361,120. However, the 17α-chloroethynyl compounds surprisingly are more effective in ovulation inhibition than are the 17α-ethynyl compounds.

The following table shows the superior efficacy of 17α-chloroethynyl-17β-hydroxy-18-methyl-11-methylene-4-estren-3-one (A) as compared with 17α-ethynyl-17β-hydroxy-18-methyl-11-methylene-4-estren-3-one (B) in the ovulation inhibition test on rats.

| OVULATION INHIBITION IN RATS AFTER SUBCUTANEOUS APPLICATION | | |
|---|---|---|
| DOSE (MG) | COMPOUND A | COMPOUND B |
| | (% INHIBITION) | |
| 0.1 | 100 | 100 |
| 0.03 | 83 | 0 |

The ovulation inhibition was determined by tubal inspection. It can be seen from the table that chloroethynyl compound A is at least three times stronger than ethynyl compound B. Beyond that A has less androgenic side effects than B.

Moreover, the higher esters of the chloroethynyl compounds of this invention are distinguished by protracted effectiveness.

Due to their strong ovulation-inhibitory effect, the compounds of this invention can be utilized with special advantage in contraceptive preparations, wherein they can be used as the progestational component in combination with an estrogenically active hormone component, such as, for example, ethynylestradiol (see, e.g., Contraception: The Chemical Control of Fertility, edited by Daniel Lednicer, 1969, Marcel Dekker, Inc. New York, whose disclosure is incorporated by reference herein), or as the sole active ingredient. However, the compounds can also be utilized in preparations for the treatment of gynecological disturbances, such as cycle irregularities in case of inadequate function of the corpus luteum, climacteric complaints, endometriosis, etc.

For pharmaceutical usage, the novel compounds can be conventionally processed, together with the additives, vehicles, and flavoring agents customary in galenic pharmacy, into the usual medicines. Especially suitable for oral administration are tablets, dragees, capsules, pills, suspensions, or solutions. Particularly suitable for parenteral application are oily solutions, e.g., sesame oil or castor oil solutions which can optionally additionally contain a diluent, such as, for example, benzyl benzoate or benzyl alcohol. The concentration of active ingredient (unit dosage) is dependent on the form of administration. Thus, for example, tablets for oral administration contain preferably 0.01–0.5 mg of active ingredient, and solutions for parenteral administration contain preferably 1–100 mg of active agent per 1 ml of solution.

The pharmacologically active compounds of Formula I can be processed in accordance with conventional methods of galenic pharmacy to provide medicinal agents to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The dosage of the pharmaceutical preparations of this invention can vary with the type and purpose of administration. For example, the daily contraceptive dosage in oral administration is 0.05–0.5 mg of the compound of Formula I, administered in the same manner as the known contraceptive agent Norinyl ® containing norethindrone and ethynylestradiol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a)

17α-Chloroethynyl-3,3-(2',2'-dimethyltrimethylenedioxy)-18-methyl-11-methylene-5-estren-17β-ol Under argon, 12.5 ml of a 5% ethereal methyllithium solution is added dropwise at about 0° C. to 2.5 ml of 1,2-dichloroethylene in 15 ml of absolute ether. After 30 minutes, 1.0 g of 3,3-(2',2'-dimethyltrimethylenedioxy)-18-methyl-11-methylene-5-estren-17-one in 30 ml. of absolute ether is added thereto, and the mixture is stirred for another 20 minutes, combined with saturated ammonium chloride solution, diluted with ether, and the solution washed with water. The crude product is recrystallized from acetone/hexane, thus obtaining 740 mg of 17α-chloroethynyl-3,3-(2',2'-dimethyltrimethylenedioxy)-18-methyl-11-methylene-5-estren-17β-ol, m.p. 214.0° C. $[\alpha]_D = -16.8°$.

(b)

17α-Chloroethynyl-17β-hydroxy-18-methyl-11-methylene-4-estren-3-one

At room temperature, 1.0 g of 17α-chloroethynyl-3,3-(2',2'-dimethyltrimethylenedioxy)-18-methyl-11-methylene-5-estren-17β-ol in 40 ml of acetone is combined with 0.5 ml of semiconcentrated hydrochloric acid. After 1.5 hours the mixture is neutralized with sodium bicarbonate solution, the mixture is extensively concentrated under vacuum, and the residue is dissolved in ethyl acetate. The crude product is purified by preparatively layer chromatography (eluent: hexane/ethyl acetate 7:3), thus obtaining 270 mg of 17α-chloroethynyl-17β-hydroxy-18-methyl-11-methylene-4-estren-3-one, m.p. 168.9° C. $[\alpha]_D = +35.6°$.

EXAMPLE 2

17β-Acetoxy-17α-chloroethynyl-18-methyl-11-methylene-4-estren-3-one 1.0 g of 17α-chloroethynyl-17β-hydroxy-18-methyl-11-methylene-4-estren-3-one is stirred in 10 ml of pyridine with 5 ml of acetic anhydride and 50 mg of 4-(dimethylamino)-pyridine for 3 hours under argon at room temperature. The solution is introduced into ice/water which contains sulfuric acid. The precipitated product is vacuum-filtered, dissolved in ethyl acetate, washed with water, and dried. Chromatography of the crude product on silica gel with acetone/hexane yields 710 mg of 17β-acetoxy-17α-chloroethynyl-18-methyl-11-methylene-4-estren-3-one as a frothy product.

EXAMPLE 3

17α-Chloroethynyl-18-methyl-11-methylene-17β-(O-tridecanoylglycoloyloxy)-4-estren-3-one Under argon, 650 mg of O-tridecanoylglycoloylchloride is added dropwise within 2 hours at 100° C. to 200 mg of 17α-chloroethynyl-17β-hydroxy-18-methyl-11-methylene-4-estren-3-one and 200 mg of 4-(dimethylamino)-pyridine in 2 ml of tetrachloroethylene. The mixture is heated for 3 hours to 80° C., allowed to cool, diluted with ether, and washed with aqueous oxalic acid solution and water to render the mixture neutral. The crude product is chromatographed on silica gel with acetone/hexane, thus obtaining 210 mg of 17α-chloroethynyl-18-methyl-11-methylene-17β-(O-tridecanoylglycoloyloxy)-4-estren-3-one as a colorless oil.

EXAMPLE 4

17α-Chloroethynyl-18-methyl-11-methylene-4-estren-17β-ol

Under argon, 7 ml of a 5% ethereal methyllithium solution is added dropwise to 1.3 ml of 1,2-dichloroethylene in 10 ml of absolute ether at 0° C. After 30 minutes, 510 mg of 18-methyl-11-methylene-4-estren-17-one in 12 ml of absolute ether is added to the reaction mixture; the latter is stirred for another 15 minutes, combined with saturated ammonium chloride solution, diluted with ether, and the solution washed with water. The crude product is chromatographed on silica gel with acetone/hexane, thus producing 360 mg of 17α-chloroethynyl-18-methyl-11-methylene-4-estren-17β-ol as an oil, after crystallization from acetone/hexane, m.p. 165.5° C. $[\alpha]_D = +17.6°$ C.

EXAMPLE 5

17β-Acetoxy-17α-chloroethynyl-18-methyl-11-methylene-4-estrene

At room temperature, 210 mg of 17α-chloroethynyl-18-methyl-11-methylene-4-estren-17β-ol in 3 ml of pyridine is combined with 10 mg of 4-(dimethylamino)pyridine and 1.5 ml of acetic anhydride. The solution is introduced into ice/water which contains sulfuric acid. After extraction with ethyl acetate, the solution is washed with water and dried. The crude product is purified by preparative layer chromatography (eluent: hexane/ethyl acetate 7:3), thus isolating 130 mg of 17β-acetoxy-17α-chloroethynyl-18-methyl-11-methylene-4-estrene as a frothy product.

EXAMPLE 6

17α-Chloroethynyl-18-methyl-11-methylene-17β-undecanoyloxy-4-estrene 6 ml is distilled off from a solution of 400 mg of undecylic acid in 40 ml of benzene. After cooling to room temperature, 0.4 ml of trifluoroacetic acid anhydride is added to the mixture, the latter is stirred for 30 minutes, and 300 mg of 17α-chloroethynyl-18-methyl-11-methylene-4-estren-17β-ol is added thereto. After 2 hours the mixture is combined with 5 ml of acetone/water (1:1), stirred for 30 minutes, and then concentrated under vacuum. The residue is taken up in methylene chloride, washed with sodium bicarbonate solution and water, and dried. The crude product is purified by preparative layer chromatography (eluent: hexane/ethyl acetate 7:3), thus obtaining 115 mg of 17α-chloroethynyl-18-methyl-11-methylene-17β-undecanoyloxy-4-estrene as an oily product.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11-methylene steroid of the formula

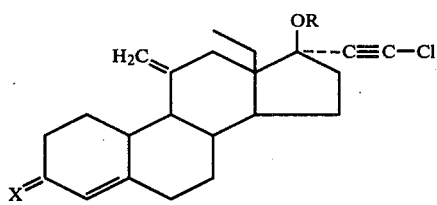

wherein

R is hydrogen or the acyl residue of a hydrocarbon $C_{1-17}$ carboxylic or sulfonic acid, and X is oxygen or two hydrogen atoms.

2. 17α-Chloroethynyl-17β-hydroxy-18-methyl-11-methylene-4-estren-3-one, a compound of claim 1.

3. 17β-Acetoxy-17α-chloroethynyl-18-methyl-11-methylene-4-estren-3-one, a compound of claim 1.

4. 17α-Chloroethynyl-18-methyl-11-methylene-17β-(O-tridecanoylglycoloyloxy)-4-estren-3-one, a compound of claim 1.

5. 17α-Chloroethynyl-18-methyl-11-methylene-4-estren-17β-ol, a compound of claim 1.

6. 17β-Acetoxy-17α-chloroethynyl-18-methyl-11-methylene-4-estrene, a compound of claim 1.

7. 17α-Chloroethynyl-18-methyl-11-methylene-17β-undecanoyloxy-4-estrene, a compound of claim 1.

8. A compound of claim 1, wherein X is oxygen.

9. A pharmaceutical composition comprising a contraceptively effective amount of a compound of claim 1 and a pharmaceutically acceptable carrier.

10. A method of inhibiting ovulation in a female which comprises administering to the female a contraceptively effective amount of a compound of claim 1.

* * * * *